United States Patent [19]

Zavy

[11] Patent Number: 5,252,564
[45] Date of Patent: Oct. 12, 1993

[54] METHOD TO DECREASE CORTISOL SECRETION BY FEEDING MELENGESTEROL ACETATE

[75] Inventor: Michael T. Zavy, El Reno, Okla.

[73] Assignee: The United States of America as represented by the Secretary of Agriculture, Washington, D.C.

[21] Appl. No.: 677,716

[22] Filed: Mar. 29, 1991

[51] Int. Cl.$^5$ ............................................. A61K 31/56
[52] U.S. Cl. ................................... 514/170; 552/528; 552/529
[58] Field of Search ................. 514/170, 147; 552/526, 552/539

[56] References Cited

PUBLICATIONS

C. A. Nugent et al., "Suppression of Cortisol by a Progestational Steroid, Melengestrol," Clinical Pharmacology and Therapeutics 18(3):338-344 (1975).

W. R. Robertson et al., "The Effect of Some Antiprostatic Steroids Upon Cortisol Production by Guinea--Pig Adrenal Cells Stimulated by ACTH," Biochem. Pharmacol. 38(21):3669-3671 (1989).

. . . , "Shipping Fever: Drive It Out!," Agricultural Research, pp. 12–13 (Mar. 1990).

James A. Roth, "Immunosuppression and Immunomodulation in Bovine Respiratory Disease," In Bovine Respiratory Disease, A Symposium, ed. Raymond W. Loan, pp. 143-192, Texas A&M University Press.

Richard L. Elton et al., "Biological Activities of Some 6-Methylated Progesterones," P.S.E.B.M., 103: 175-177 (1960).

R. D. Randel et al., "Effect of Melengestrol Acetate on Plasma Progesterone, Luteinizing Hormone and Total Corticoids in Dairy Heifers," J. Animal Science 35(2): 389-397 (1972).

Gordon W. Duncan et al., "Biologic Effects of Melengestrol Acetate," Fertility & Sterility, 15(4): 419-432 (1964).

G. R. McKinney et al., "The Adrenal Responses to Stress of Rats Treated with Certain Progestagens," Abstract, Fourth Annual Meeting, Toxicol. Appl. Pharm., 7: 491 (1965).

Deborah J. Middleton et al., "Suppression of Cortisol Responses to Exogenous Adrenocorticotrophic Hormone, and the Occurrence of Side Effects Attributable to Glucocorticoid Excess, in Cats During Therapy with Megestrol Acetate and Prednisolone," Can. J. Vet. Res., 51: 60-65 (1987).

R. C. Upadhyay et al., "Studies on the Effects of Liv. 52 and Melengesterol Acetate (MGA) on Body Weights and Certain Blood Constituents of Poultry," Chem. Abstr. 104: 50259c, pp. 463-464 (1986).

M. N. Sillence et al., "Age- and Sex-Dependent Stimulation of Growth Rate in Rats by the Adrenal Inhibitor Trilostane", J. Endocr. 113: 479-484 (1987).

M. N. Sillence et al., "Effects of Trenbolone Acetate and Testosterone on Growth and on Plasma Concentrations of Corticosterone and ACTH in Rats," J. Endocr., 126: 461-466 (1990).

M. N. Sillence et al., "Effects of Metyrapone and Etomidate on Adrenal Function and Growth Rate in Female Rats," J. Endocr., 113: 473-478 (1987).

(List continued on next page.)

Primary Examiner—Frederick E. Waddell
Assistant Examiner—K. Weddington
Attorney, Agent, or Firm—M. Howard Silverstein; Randall E. Deck; John D. Fado

[57] ABSTRACT

A method for decreasing the adrenal secretion of glucocorticoids, especially cortisol, in male livestock without substantially suppressing the animal's immune system by oral or other administration of effective doses of melengesterol acetate (MGA) or derivatives thereof. Ideally, the MGA may be used in admixture with the subject animal feed, although it is understood that the compound may be administered separately.

12 Claims, 9 Drawing Sheets

OTHER PUBLICATIONS

R. B. Buckland et al., "Effect of Feeding Chlorpromazine, Metyrapone and Pargyline to Chicks on Plasma Corticoid Levels and the Effect of Stress on Their Relationship to Body Weight," Poult. Sci., 52: 1215–1217 (1973).

A. R. Ezzat, "Enhancement of the Adrenocortical Response to Metyrapone by L–Dopa in the Chicken (*Gallus domesticus*)," Brit. Poult. Sci., 29: 167–170 (1988).

G. Colmano et al., "Effect of Metyrapone and DDD on Infectious Diseases," Poult. Sci. 50: 850–854 (1971).

Walter B. Gross, "Effect of Adrenal Blocking Chemicals on Viral and Respiratory Infectious of Chickens," Can J. Vet. Res., 53: 48–51 (1988).

D. L. Thompson et al., "Cell-Mediated Immunity in Marek's Disease Virus-Infected Chickens Genetically Selected for High and Low Concentrations of Plasma Corticosterone," Am. J. Vet. Res. 41(1): 91–96 (Jan. 1980).

P. Thaxton et al., "Modification of High Temperature and ACTH Induced Immunodepression by Metyrapone," Poult. Sci. 52: 618–624 (1973).

METHOD TO DECREASE CORTISOL SECRETION BY FEEDING MELENGESTEROL ACETATE

BACKGROUND OF THE INVENTION

1. Field of the Invention

The invention relates to a method to control the adrenal secretion of glucocorticoids in male livestock without impairing the animal's immune response.

2. Description of the Prior Art

Bovine respiratory disease complex (shipping fever) has long been recognized as a multifactorial condition of calves and adult cows involving the combination or management, stress, viral, and bacterial factors [Hoerlein et al., J. Am. Vet. Med. Assoc., 131: 123-127, (1957); Roth, "Immunosuppression and Immunomodulation in Bovine Respiratory Disease", In: R. W. Loan (ed.), Proceedings of the North American Symposium on Bovine Respiratory Disease, Texas A&M University Press, College Station, (1983), pages 143-192; and Filion et al., Can. J. Comp. Med., 48: 268-274, (1984)]. Calves are rendered susceptible to the disease complex as a result of suppression of the animal's immune system. The organism responsible for the acute fibrinous pneumonia associated with this disease complex is usually *Pasteurella hemolytica,* which is a normal resident of the nasal microflora. In stressed calves this microorganism can proliferate and subsequently colonize in the lower respiratory tract.

Major factors which account for the immunosuppression are viral and/or stress related. Elevated levels of glucocorticoids and especially cortisol resulting from stress have been found to suppress several aspects of the immune system in cattle [Roth, "Cortisol as Mediator of Stress-Associated Immunosuppression in Cattle", In: G. Moberg (ed.), Animal Stress, Waverly Press, Baltimore, (1985), pages 225-243] and other animals.

Progesterone has been shown to have antiglucocorticoid activity in vitro in rats and mice [Naylor et al., Endocrinol. 107: 117-121 (1980) and J. Steroid Biochem. 14: 1303-1309 (1981); Grunfeld et al., Hypertension 7: 292-299 (1985); and Stevenson et al., Int. J. Immunopharmac. 10: 1-6 (1988)]. In cattle, Capuco et al. [Proc. Soc. Exp. Biol. Med. 164: 386-393 (1980)] have demonstrated that progesterone could block binding of the synthetic glucocorticoid, dexamethasone, to the glucocorticoid receptor in mammary tissue. Synthetic progestins including 6-β-bromoprogesterone [Naylor (1980), ibid.] and RU 486 [Bertagne et al., J. Clin. Endocrinol. 59: 25-28 (1984)] have also been found to have antiglucocorticoid activity in the rat and human, respectively. Other, 6-methylated progestins have been shown to possess adrenal depressant activity [Elton et al., Proc. Soc. Expt. Biol. Med. 103: 175-177 (1960)], while Middleton et al. [Can. J. Vet. Res. 51: 60-65 (1987)] found that megesterol acetate reduced cortisol secretion in cats. May et al. [Life Sci. 46: 1627-1631 (1990)] showed that dehydroandrosterone (DHEA) administration could antagonize the effect of glucocorticoids and would prevent thymic involution normally induced by glucocorticoids.

A commonly used synthetic progesterin which is used extensively in female cattle to suppress estrus is melengesterol acetate (MGA), fed at a rate of 0.25 to 0.50 mg/head/day. Administration of very high pharmacological levels of the compound has demonstrated adrenal corticoid-like activity, with inhibition of the inflammatory response in rats [Duncan et al., Fertil, Steril. 15: 419-432 (1964)]. McKinney et al. [Toxicol. Appl. Pharm. 7:491 (1951)] found that MGA reduced glucocorticoid levels in stressed female rats fed very high doses of the compound. However, upon oral administration of lower doses to dairy heifers, MGA did not exhibit any effect on total corticoid levels [Randel et al., J. Animal Sci. 35: 389-397 (1972)]. In later work, Upadhyay et al., showed that feeding MGA to poultry did not affect body weight gains [Indian J. Anim. Res. 18: 94-98 (1984)].

SUMMARY OF THE INVENTION

I have now surprisingly found that melengesterol acetate and derivatives thereof are effective for controlling adrenal secretion of glucocorticoids such as cortisol in male livestock without impairing immune response. The compound may be orally or otherwise administered to the livestock at a dosage effective to substantially decrease the secretion of cortisol below normal basal levels, and with substantially no suppression of the animal's immune system. Further, the dosage should not be so high as to prevent secretion of elevated levels of cortisol during periods of extreme stress. However, the amount of cortisol secreted in these situations will still be less than that found in untreated livestock.

In accordance with this discovery, it is an object of this invention to provide a method for controlling the basal and stress-induced adrenal secretion of glucocorticoids in male livestock without compromising the immune system.

A further object of this invention is to provide a method for decreasing the stress-induced hypersecretion of glucocorticoids in livestock such as by shipping. The suppression of the animal's immune system accompanying elevated glucocorticoid levels may thus be substantially reduced or prevented.

Another object of this invention is to provide a method for decreasing the cortisol secretion of castrated livestock to substantially diminish the rate of tissue or muscle breakdown and enhance growth.

Yet another object is to provide a method for controlling cortisol secretion which has only a transitory effect, allowing return to normal adrenal function after cessation of the administration of melengesterol acetate.

Other objects and advantages of the invention will become obvious from the ensuing description.

DETAILED DESCRIPTION OF THE INVENTION

Figure 1:
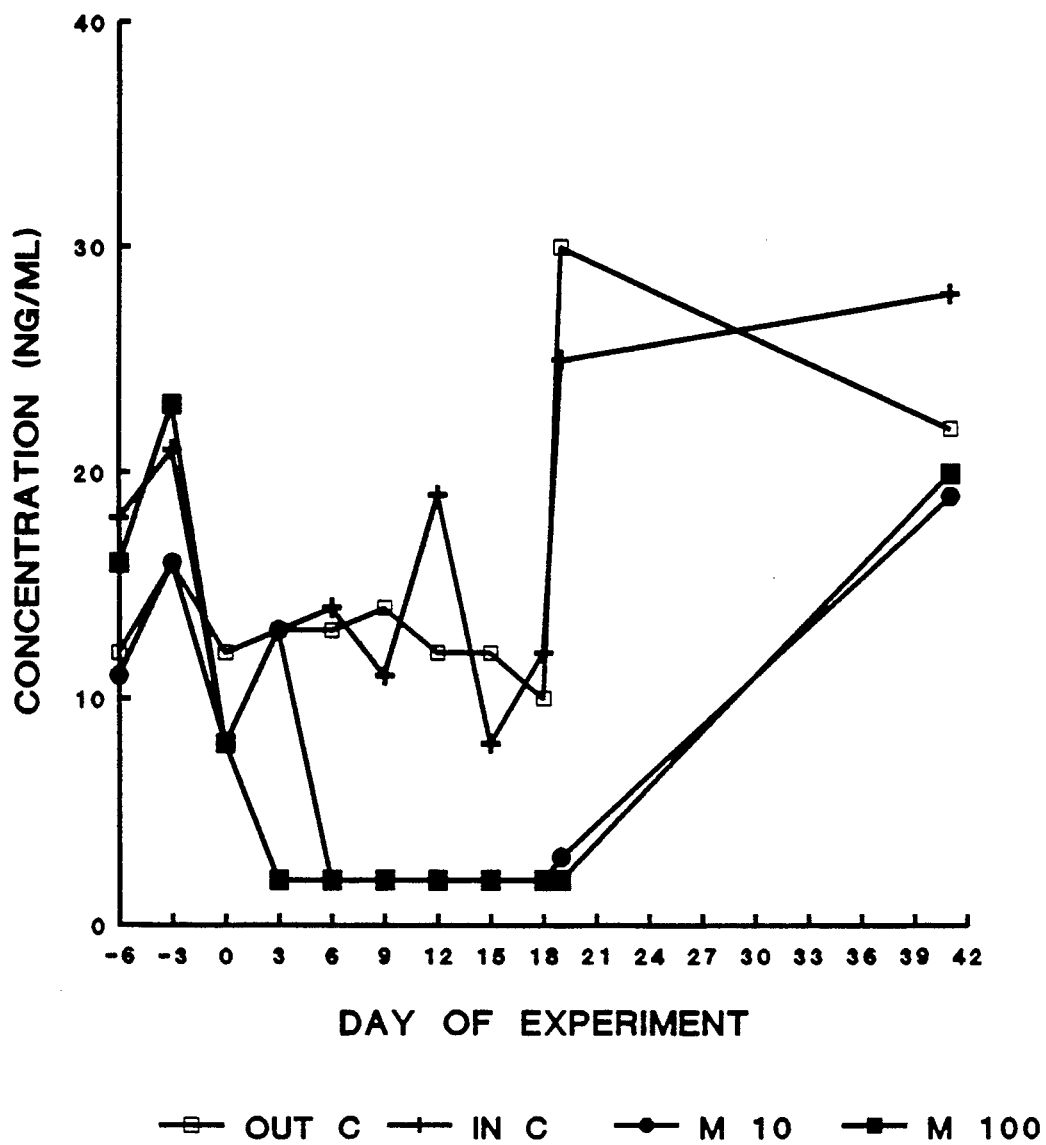
FIG. 1 shows basal cortisol levels of beef steers in Example 1.

In chronic situations, excessive secretion of cortisol can cause wasting of soft tissue such as muscle, and immunocompromise animals in times of stress. Excessive secretion of cortisol in stress-induced cattle, for example, is believed to be a major predisposing factor in the contraction of bovine respiratory disease complex, a disease which has been estimated to cost American cattle produces in excess of 400 million dollars per year. Elevated basal levels of cortisol, such as is found in castrated males in comparison to non-castrated males, may also lead to tissue or muscle breakdown.

According to this invention, there is provided a method for decreasing the adrenal secretion of glucocorticoids, especially cortisol, in male livestock, especially castrated livestock, without substantially suppressing the animal's immune system by administration of effective doses of melengesterol acetate (MGA) or derivatives thereof. Ideally, the MGA may be orally administered such as in admixture with the subject animal's feed, although it is understood that the compound may be administered separately, orally or otherwise (e.g., injection, sustained release bolos, implants, microencapsulation, etc.).

The method of the invention may be used for the treatment of male livestock, particularly bovine (including calves, adults and steers), pigs, and sheep (including lambs and wethers).

An effective dose is defined herein as an amount sufficient for substantially lowering the basal adrenal secretion of glucocorticoids, especially cortisol, in comparison with untreated livestock, without substantially suppressing the immune system of the subject animal. In the preferred embodiment, the dosage is selected to lower *but not prevent* the secretion of the glucocorticoids, thereby allowing the subject animals to respond to conditions of extreme stress with secretion of elevated levels of the glucocorticoids. In these conditions, elevated concentrations of cortisol may still be produced, but at a lower level than that produced by untreated animals, and produced over a shorter period of time. However, the hypersecretion of cortisol over a long period of time in response to a series of less severe stresses is no longer found.

Suitable doses may be readily determined by the practitioner skilled in the art and will vary somewhat with the size of the animal, the degree of suppression of adrenal glucocorticoid secretion desired, method of administration, and the activity of the melengesterol acetate derivative (is used). The oral administration of melengesterol acetate by feeding in the range of about 1 to about 50 mg/head/day is preferred, with a range of about 1 to about 10 mg/head/day being particularly preferred base upon data with bovine. The practitioner skilled in the art will recognize that lower doses may be effective using other techniques of administration (i.e., sustained release bolos). Amounts greater than 50 mg/head/day may unduly restrict or even prevent glucocorticoid secretion and may damage the animal's adrenal gland. At higher amounts, the MGA may also exhibit glucocorticoid-like activity, suppressing the animal's immune response. Higher doses may also require longer adrenal recovery periods. It is anticipated that the desired resting or basal, non-stressed (acclimated) cortisol levels in blood should be about 1 ng/ml to about 30 mg/ml and especially about 1 ng/ml to about 20 ng/ml for bovine. While preferred levels may vary for other animals, the appropriate levels may be readily determined by the practitioner skilled in the art.

Administration of MGA to the livestock in accordance with the invention may be at any time and continued for as long as lowering of glucocorticoid levels is desired. In situations where this lowering is for the purpose of reducing hypersecretion in response to stress, the MGA may be administered about 1 to about 7 days prior to the anticipated stress, preferably about 5 to about 7 days, and continued until the stress is removed. Examples of situations wherein MGA may be administered prior to anticipated stress include but are not limited to shipping, castration, dehorning, weaning, handling, and forced exercise.

Melengesterol acetate and its derivatives are synthetic progesterins which are well known and readily available. Suitable derivatives may be readily determined by the practitioner skilled in the art, and include but are not limited to medroxy progesterone acetate. The compounds may be used alone or in conjunction with any compatible, commercially available pharmaceutical carrier.

EXAMPLE 1

Twenty two cross-bred beef calves (steers), which were healthy and clinically free of disease and weighing approximately 227 kg, were used to study the effects of melengesterol acetate (MGA) on basal and stress-induced glucocorticoid levels. Six calves were assigned to each of the following treatment groups: (1) 10 mg MGA/head/day, (2) 100 mg MGA/head/day, and (3) an inside control. Four calves which were not subjected to confinement were assigned to an outside control group (4). Calves were assigned to two different locations in a randomized complete block design with repeated measurement. The study was divided into three periods: (a) a one-week pretreatment (days −6 to −1) where calves did not have a stress or a treatment; (b) a two-week treatment period (days 0 to 14) where MGA was fed to calves in the first two treatment groups, and where the calves were stanchioned to provide a confinement stress; and (c) a transit period (day 15) where the calves were subjected to a 10-hour transport (shipping) stress, followed by their release to conditioning lots for post-transit evaluation. Treatments with MGA were discontinued after day 14, just prior to transport.

To evaluate the stress-induced response of the adrenal glands, 100 IU of adrenal corticotropin hormone (ACTH), a pituitary hormone that stimulates adrenal secretion of glucocorticoids, was administered to all animals as an intravenous bolus at day −1 at the end of the pretreatment period (PRETR), at day nine of the treatment period (TRT), day 15 just prior to treatment (PRETN) and following transport (TRANS), and at day 36 following a three-week recovery period (RCVRY). Blood samples were obtained prior to ACTH administration (time 0 which was the basal sample on these days) and at 60, 120, 180, 240, and 360 min thereafter. Blood samples were analyzed for cortisol concentration by a specific radioimmunoassay which did not cross-react with either MGA or progesterone or any other related corticoid compound.

Blood samples were also collected without ACTH administration, and assayed in the same manner to determine basal cortisol levels at three-day intervals from the beginning of the experiment through the transit period.

FIG. 1 demonstrates basal cortisol levels in the calves in each group. This data indicates that MGA fed at high levels (100 mg/head/day) results in a rapid decline in cortisol secretion, whereas lower levels of MGA (10 mg/head/day) resulted in a similar decrease in basal cortisol levels but the onset of the decline was slower. In each group, adrenal function, as evidenced by basal cortisol secretion, is back to normal by three weeks after drug treatment. However, it is quite possible that recovery occurred prior to this, particularly with the lower dosage of MGA.

Figure 2:
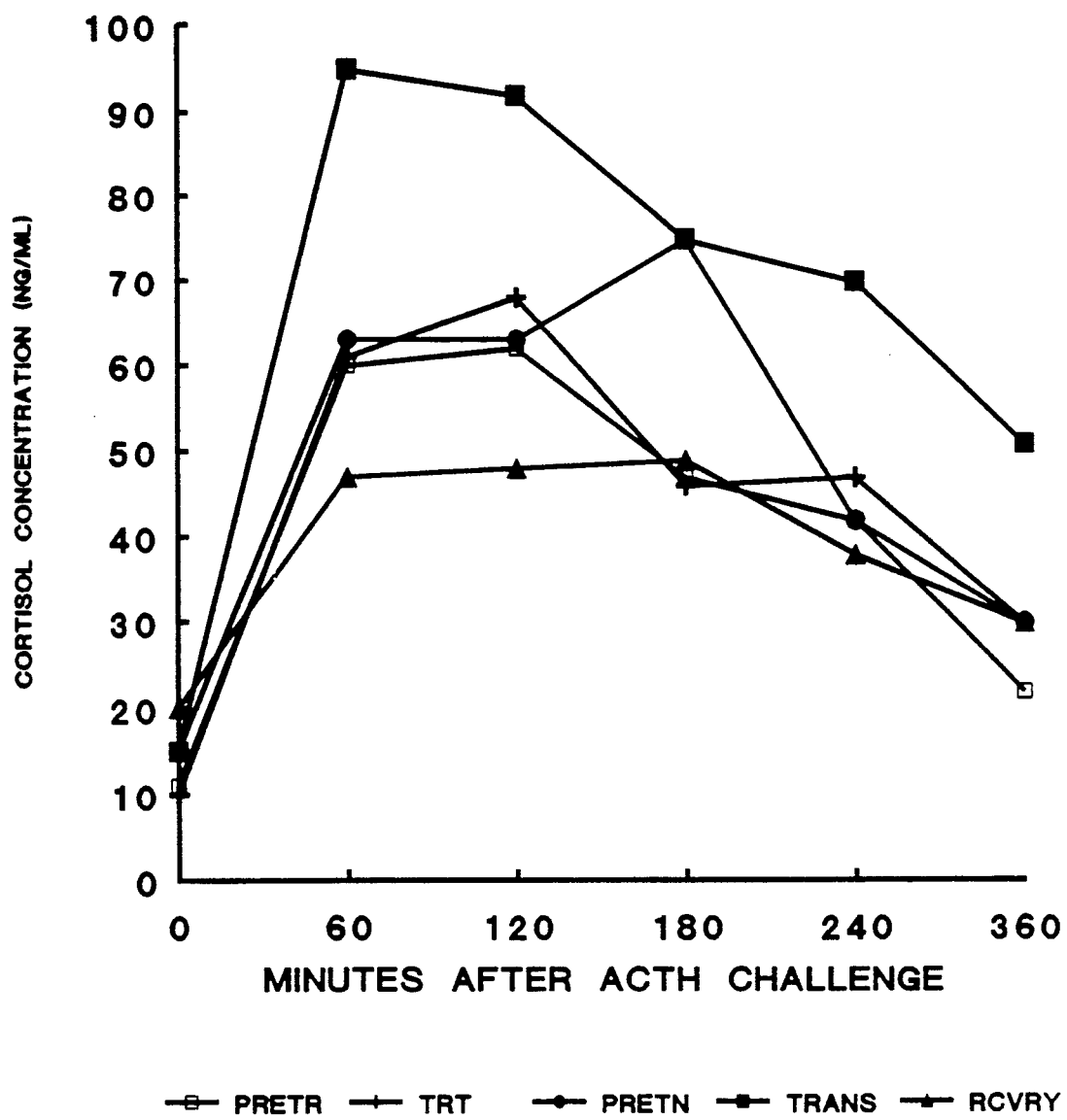
FIGS. 2-5 show cortisol secretion in beef steers in response to challenge with ACTH in Example 1.
Figure 3:
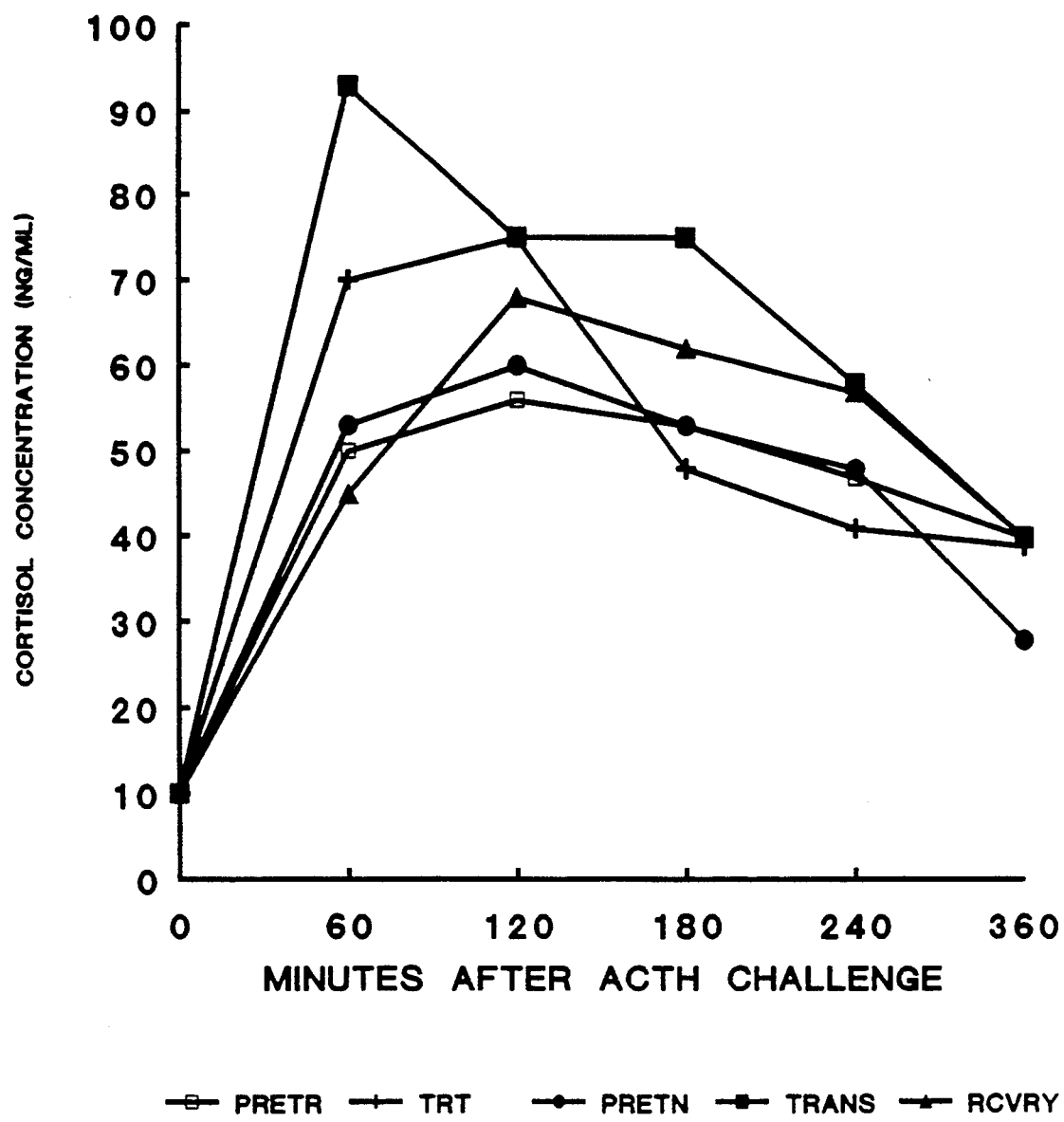

FIGS. 2–5 show the cortisol secretion in response to the ACTH challenge in the outside control group, inside control group, the group receiving 100 mg MGA/head/day, and the group receiving 10 mg MGA/head/day, respectively. FIGS. 2 and 3 demonstrate that steers in the control groups exhibited very similar cortisol secretion in response to ACTH challenge during each measurement. The figures also show that transportation elicits a greater amount of cortisol release than the other periods, and is thus considered to be a severe stress to the steers.

Figure 4:
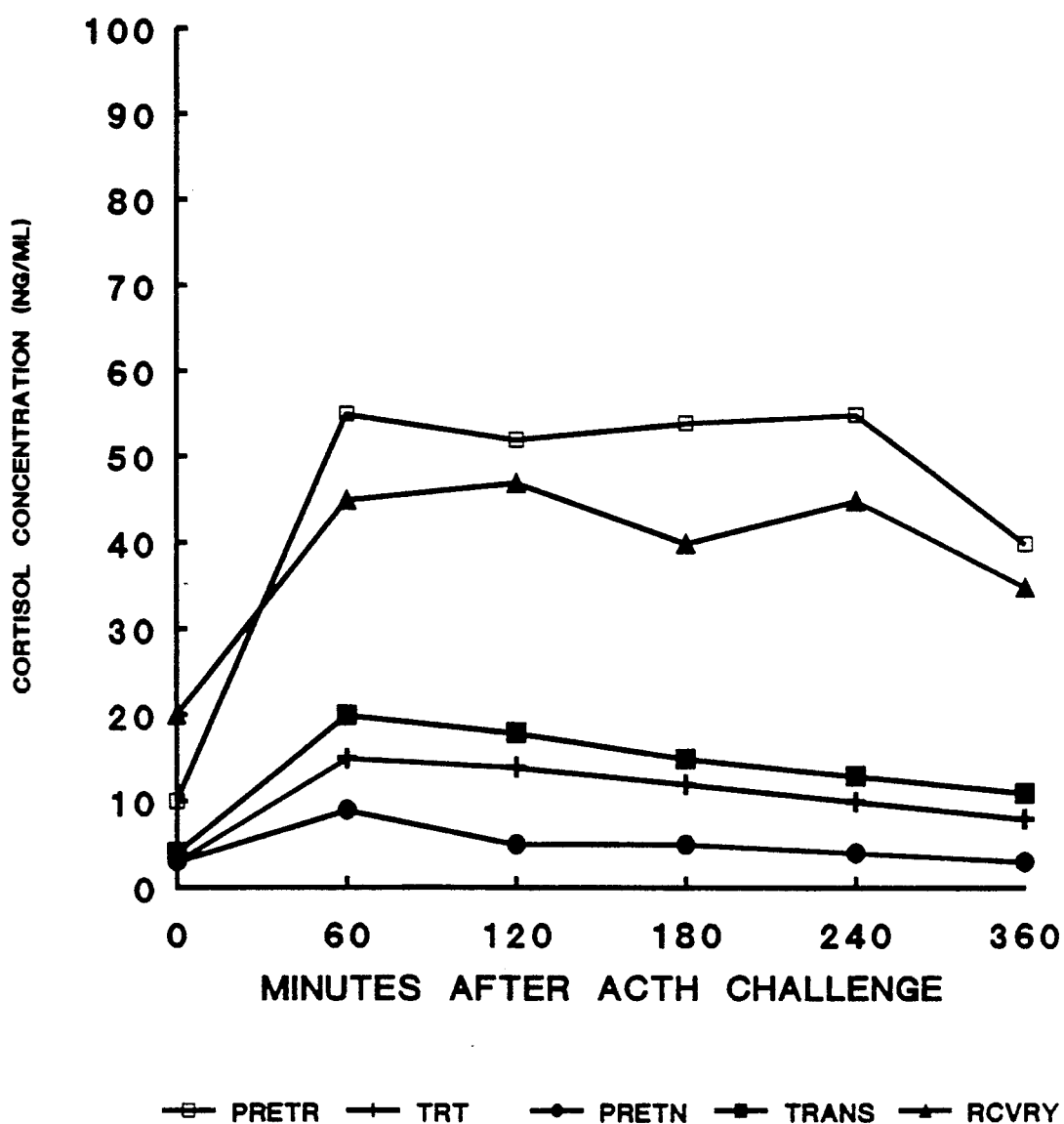
Figure 5:
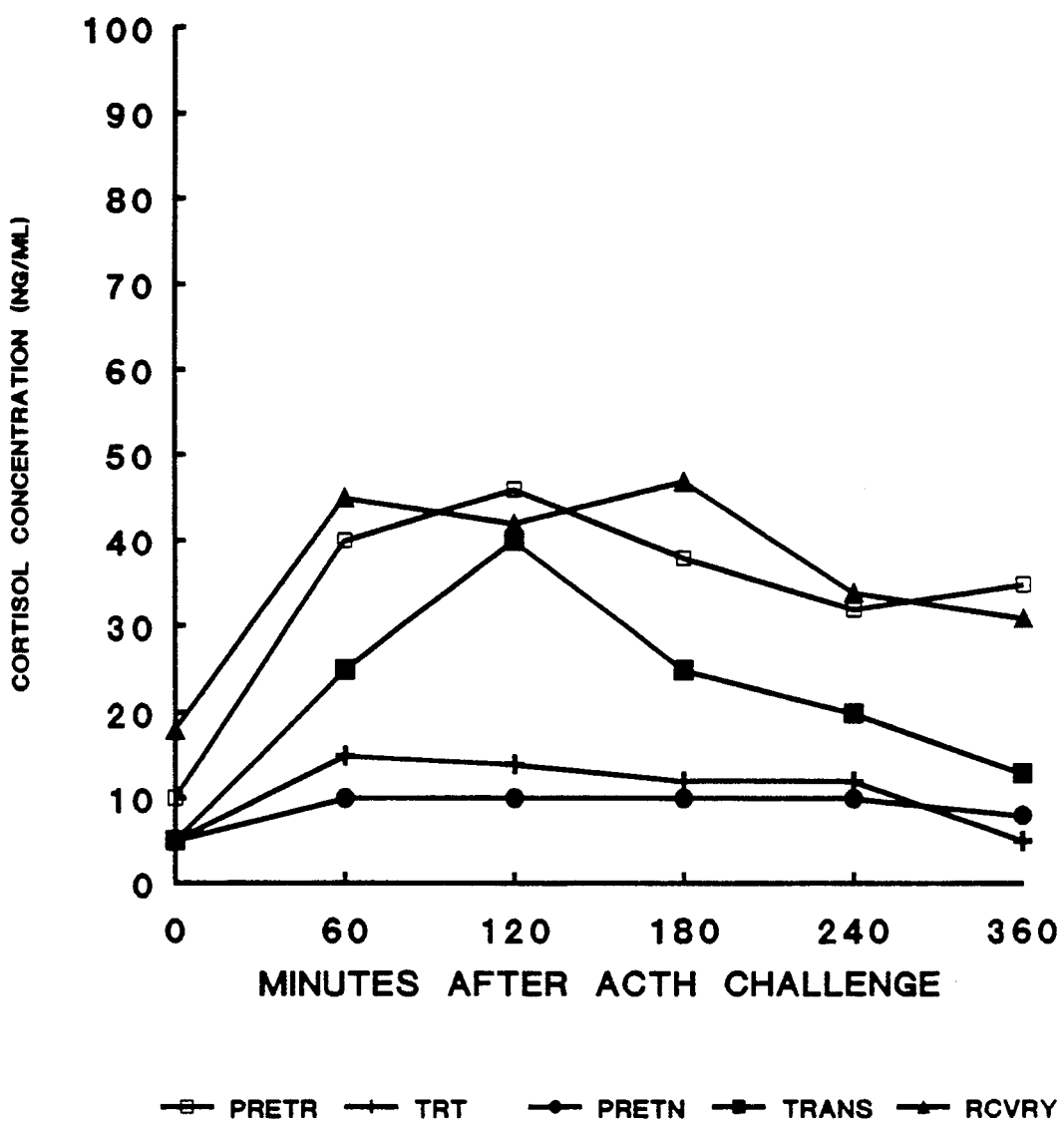

The effect of MGA on ACTH is shown in FIGS. 4 and 5. The pretreatment cortisol profiles in each group are very similar to that seen in the control groups. However, MGA feeding resulted in a dramatic depression during the treatment and pretransportation periods. During the transportation period, cortisol secretion varied substantially with the level of administered MGA. In the 100 mg group, steers subjected to transportation, which is a severe stress, did not elicit a substantial secretion of cortisol in response in response to ACTH, and the values were only slightly higher than those seen during the treatment and pretransportation periods. In the 10 mg group, the steers subjected to transportation did exhibit a significant cortisol increase which was greater than that which occurred in the 100 mg group, but was still about $2\frac{1}{2}$ times less than the peak of cortisol in either of the control groups. Whereas the 100 mg dose of MGA almost entirely suppresses cortisol secretion, the 10 mg dose only restrains it. In each group, cortisol secretion is back to pretreatment levels by three weeks into the recovery period.

EXAMPLE 2

Thirty cross-bred beef calves (steers), which were healthy and clinically free of disease and weighing approximately 227 kg, were used to study progesterone and melengesterol acetate (MGA) for their effects upon immune response associated with confinement and transport stress. Six calves were assigned to each of the following treatment groups: (1) 1 mg MGA/head/day, (2) 10 mg MGA/head/day, and (3) 50 mg/head/day progesterone ($P_4$), (4) an inside control, and (5) an outside control (calves which were not subjected to confinement). Calves were assigned to two different locations in a randomized complete block design with repeated measurement. The study was divided into three periods: (a) a one-week pretreatment (days −6 to −1) where calves did not have a stress or a treatment; (b) a two-week treatment period (days 0 to 14) where MGA was fed to calves in the first two treatment groups, and where the calves were stanchioned to provide a confinement stress; and (c) a transit and post-transit period (day 15 and on) where the calves were subjected to an 8-hour transport (shipping) stress, followed by their release to conditioning lots for post-transit evaluation. Treatments with MGA were discontinued after day 14, just prior to transport.

Blood samples were obtained from calves by venipuncture twice during the pretreatment, treatment periods, and following the transit period. These blood samples were evaluated for WBC, RBC, PVC, differential blood counts, lactate, pyruvate, and glucose. This blood was also a source of lymphocytes in which response to the lectins concavalin A, phytohemagglutinin and pokeweed mitogen was assessed. Lymphocytes from this pool also served as autologous cells in a mixed lymphocyte reaction. Polymorphonuclear cells were also obtained for antibody-dependent cell-mediated cytotoxicity (ADCC) assays.

Just before transit all calves were injected with Brucella strain 19 and blood samples were taken on days 0, 3, 7, 11, and 14. Blood serum was evaluated for anti-brucella IgM and IgG. Lymphocytes obtained at the same time were evaluated for cell-mediated response in the presence of heat-killed brucella antigen.

Animal weights were obtained 5 times during the experiment during pretreatment, before transit, after transit, and twice during the recovery period at 14 and 21 days following transport as a determinant of animal response to the applied stressors.

WBC, RBC, and Differential Blood Cell Counts

After blood was obtained, samples were collected for RBC and WBC analysis. Enumeration of cells was carried out using an electronic counter (Model ZM, Coulter Electronics, Inc., Hialeah, Fla.). Blood smears were prepared on slides for staining (Wright's) and differential leukocyte cell counting by routine light microscopy. Blood which was to be the source of red and white blood cells was collected in EDTA tubes.

Lymphocyte Blastogenesis

Blood samples were taken from calves twice during each of the following periods: pretreatment, treatment/confinement, and post-transit. Blood was then diluted 1:1 using Hanks Balanced Salt Solution (HBSS, Gibco, Grand Island, N.Y.) and layered onto Ficoll/Hypaque (sp. 1.077, Sigma Chemicals, St. Louis, Mo.). After centrifugation at 2000 g for 30 min. the mononuclear fraction was aspirated and washed 3 times in HBSS. Cell numbers were evaluated by using an electronic counter. Cells were adjusted to a final concentration of $1.0 \times 10^7$ viable cells per ml in RPMI 1640 medium (Gibco); supplemented with 5% heat-inactivated and filtered fetal calf serum (FCS, Gibco), 100 units of penicillin, and 100 $\mu$g streptomycin per ml (Gibco). Cells ($5.0 \times 10^5$) were seeded in triplicate wells of microtest tissue culture plates (Costar Plastics; Cambridge, Ma.) and incubated for 48 hr at 37° C. in 5% $CO_2$ with or without mitogen as indicated below. Six hours prior to the collection of cells, 0.5 uCi of $^3$H-Thymidine (sp. act.=2.0 Ci/$\mu$mol; New England Nuclear, Boston, Ma.) in 50 $\mu$l media was added to each well. Cells were transferred to glass microfiber filters using a Cell Harvester (Cambridge Technology, Inc., Waterton, Ma.), and $^3$H activity was determined by liquid scintillation counting (Model B3255, Packard Instrument Co., Downers Grove, Ill.).

Antibody-Dependent Cell Cytotoxicity (ADCC)

Polymorphonuclear cells (PMN) were isolated from the erythrocyte pellet obtained following Ficoll/Hypaque separation. Erythrocytes were lysed by adding buffered ammonium chloride for 6 min at room temperature. Remaining cells were rinsed 3 times in HBSS and resuspended in RPMI 1640 medium with 5% FCS. Cell numbers were determined by using an electronic counter. After counting, cells were diluted to a concentration of $2.5 \times 10^6$ cells/ml. Chicken red blood cells (CRBCs, Pel-freeze, Rogers, Ariz.) were washed and diluted to $1.0 \times 10^7$ cells/ml. Cells ($1.0 \times 10^7$ or 1 ml) were pelleted and incubated in 0.1 mCi sodium chromate ($^{51}$Cr, sp. act.=409–605 mCi/mg; New England Nuclear) for 2 hr at 37° C., then washed three times in RPMI 1640 and resuspended to a final concentration of $2.5 \times 10^5$ cells/ml.

Polymorphonuclear cells (PMN), obtained as previously described, were plated at $2.5 \times 10^6$ in cells/ml and 100 µl aliquoted into each well or 96 well U-bottom plates (Costar Plastics). The effector to target ratio was 10:1. Bovine anti-chicken serum and $^{51}$Cr-labeled CRBC (50 µl) were added to all samples, which were run in triplicate. Controls consisted of effectors and target cells without antibody. In controls, total release of $^{51}$Cr was determined by treating erythrocytes with 2N HCl. Culture plates were then centrifuged at 40 g for 2 min, incubated for 3 hr at 37° C. in a humidified atmosphere containing 5% $CO_2$ and 95% air, and then recentrifuged at 500 g for 10 min. A supernatant fraction (100 µl) from each well was aspirated and the cpm of $^{51}$Cr released determined in a gamma scintillation counter. Total counts incorporated were determined in 50 µl of $^{51}$Cr-labeled CRBC. Spontaneous release was determined by incubating $^{51}$Cr-labeled CRBC with medium alone. The amount of $^{51}$Cr released by target cells with antibody alone or target cells in the presence of effectors without antibody was not significantly different from spontaneous release. The percentage of cytotoxicity was determined by the formula:

$$\frac{CPM\ \text{effectors with antibody} - CPM\ \text{effectors without antibody}}{CPM\ \text{total incorporated} - CPM\ \text{spontaneous release}} \times 100$$

Mitogen Preparation

The following mitogens were utilized: pokeweed mitogen (PWM, Gibco), phytohaemagglutinin P (PHA, Wellcome Diagnostics, Beckingham, England), and concanavalin A type IV (Con A, Sigma). Optimal concentration of each mitogen was selected based upon previous titration profiles with peripheral blood lymphocytes.

The concentration of each mitogen produced maximal (6.4 µg/ml, 6.4 µ/ml, and 1.6 µg/ml, for PWM, PHA, and Con A, respectively) stimulation of the cells. Mitogens were added at the initiation of lymphocyte cultures in 50 µl aliquots. Proliferation responses of bovine peripheral blood lymphocytes to each mitogen were measured by $^3$H-thymidine incorporation.

Mixed Lymphocyte Reaction

Peripheral blood lymphocytes were co-cultured in triplicate with mitomycin C treated BL-3 cells ($0.5 \times 10^7$ cells/ml) [Romano et al., Vet. Immunol. Immunopath. 23: 293–307 (1989)]. Mitomycin C treatment was according to Swain [Mitomycin C, In: Selected Methods of Cellular Immunology, S. M. Shiigi et al. (ed.), W. H. Freeman, San Francisco, pp. 240–241 (1980)]. Responders and stimulators were mixed in 2:1 ratio (50 µl of $1 \times 10^6$ to 50 µl of $0.5 \times 10^6$). Cells were cultured for 72 hr in 150 µl of RPMI 1640 media with 5% FCS, 100 units of penicillin, 100 µg streptomycin per ml, and 0.05 mM mercaptoethanol in a gaseous atmosphere (5% $CO_2$ in air, 37° C.). Six hours prior to harvest 0.5 uCi $^3$H-thymidine was added to each well. Cells were harvested and counted as previously described.

Anti-Brucella IgG and IgM Antibody

A double sandwich enzyme-linked immunosorbent assay (Elisa) was used to analyze serum anti-brucella antibodies [Vos et al., Ann. N.Y. Acad. Sci. 320: 518–534 (1979); Voller et al., The Enzyme Linked Immunosorbent Assay (ELISA), Dynatech Laboratories, Inc., Va., pp. 1–44 (1979)]. Polystyrene 96 well plates (Dynatech Laboratories, Inc., Chantilly, Va.) were coated with brucella antigen (5.0 µg/ml protein, 300 µl each). Serum samples were diluted 1:100 for IgM and IgG determination. Peroxidase-labeled goat anti-bovine IgG or IgM (Kirkgaard Perry Labs, Inc., Gaitherberg, Md.) were diluted 1:1000. The results have been expressed as change in optical density 15 min after the addition of substrate (absorbers at 490 rm, t=15 min). Unsensitized bovine sera was used as a negative control.

Brucella Cell-Mediated Response

Lymphocyte blastogenic response to *B. abortus* antigen was evaluated by the method of Kaneen et al. [Vet. Immunol. Immunopathol. 4: 375–385 (1983)]. Briefly, blood mononuclear cells were separated as above and counted. Cells were then suspended to a concentration of $1.0 \times 10^6$ cells/ml. Cells were cultured in supplemented RPMI 1640 media with brucella stain 19 heat-killed vaccine. Cultures were incubated at 37° C. in a 5% $CO_2$, 95% air atmosphere for 5 days. Cultures were then pulsed with $^3$H-thymidine (sp. act.=2 Ci/µmol) for 18 hr, harvested, and counted as previously described.

Lactate, Pyruvate, and Glucose

Blood was taken during each of the phases of the experiment; two ml of blood was mixed with 4 ml of 8% perchloric acid and centrifuged. The resultant plasma was transformed to cyrotubes and kept at −80° C. until analyzed. Lactate and pyruvate were measured by the difference in the appearance or disappearance of NADH or NAD utilizing commercially available kits (Sigma Chemicals). Glucose was determined in plasma obtained at the same time periods from blood collected in sodium fluoride. Glucose was analyzed colorimetrically by the reaction of generating peroxide with glucose oxidase and the subsequent oxidation of o-dianisidine using a commercially available kit (Sigma Chemicals).

Lactate, pyruvate, and glucose were measured on a Beckman DU-50 spectrophotometer at 340 nm.

Statistical Analysis

Data was analyzed using analysis of variance procedures according to the General Linear Models of the SAS package release 6.03 (SAS, 1984).

Weight changes were analyzed in relation to feed intake, average daily gain, and feed efficiency once during the pretreatment period and twice during the treatment and post-transit periods. The analysis included main effects of location and treatment which were tested using location X treatment as the error term.

Hematological parameters including: RBC, WBC, PCV, neutrophils, lymphocytes, neutrophil:lymphocyte ratio, eosinophils, and monocytes were analyzed twice during the pretreatment, treatment and post-transit periods. The statistical model included location, treatment, period, time within period, and all appropriate 2- and 3-way interactions. Effects of treatment were tested using treatment X location as the error term, and effect of period was tested using location (treatment X period) as the error term. This model was also used for the analysis of immune response parameters which included: lymphocyte blastogenesis; mitogen stimulation by PWM, PHA and Con A; ADCC and blood metabolite parameters including: glucose, lactate, pyruvate, and lactate:pyruvate ratio.

Specific antibody response (IgM and IgG) and the ability to stimulate proliferation of peripheral lymphocytes in response to Brucella was monitored on days 0, 3, 7, 11, and 14 after initial injection of the antigen, which was at the end of the treatment period just prior to transportation. Data were evaluated by an analysis of variance in which the statistical model included location, treatment, and day as variance components.

Effects of treatment were tested using treatment X location as the error term, and effect of day was tested using treatment X time as the error term.

RESULTS

Weight Changes

Figure 6:
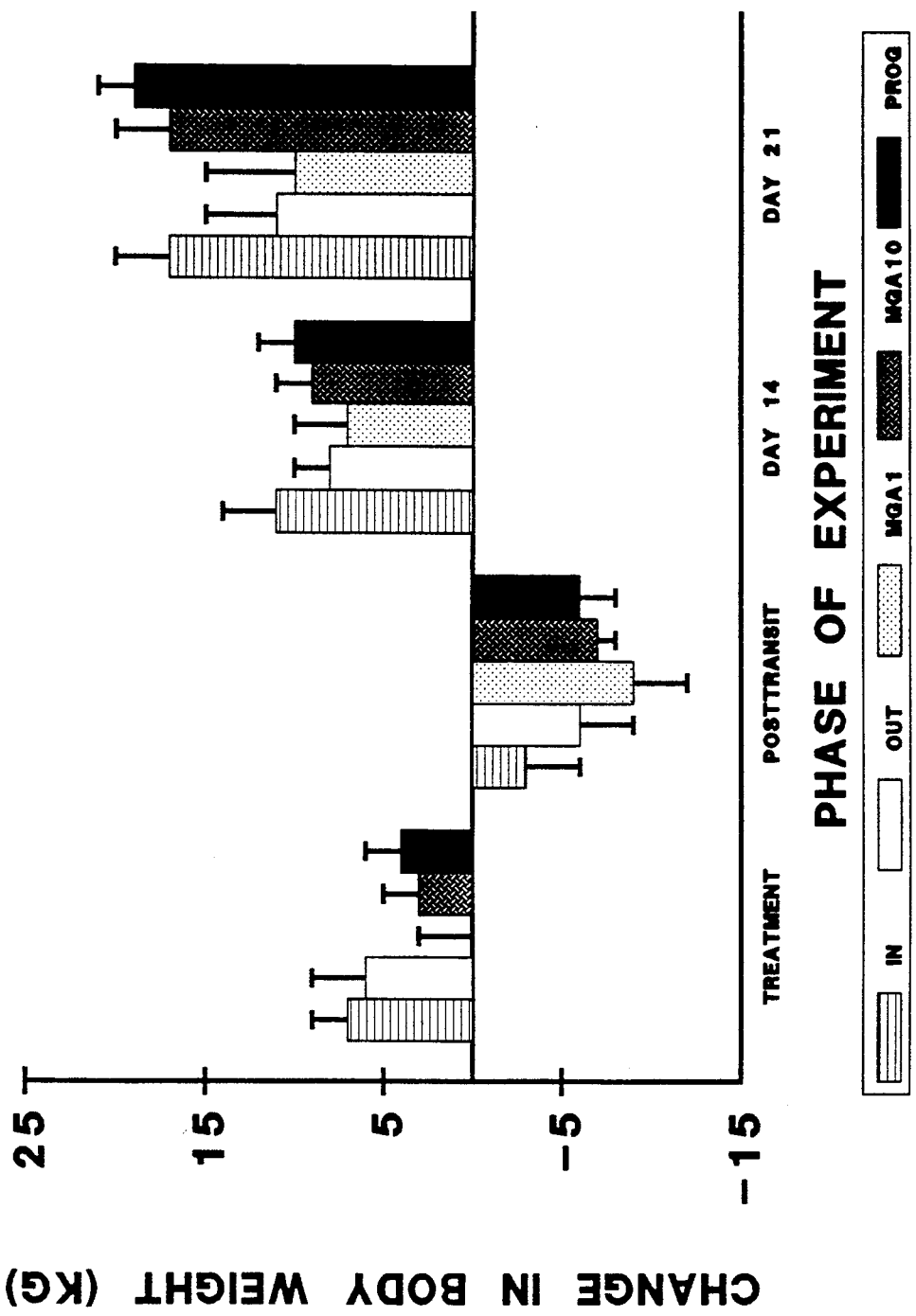
FIG. 6 shows the effect of confinement and transportation stress on change in body weight in Example 2.

There was no significant effect of treatment or a treatment X period interaction on eight change, feed intake, or feed efficiency over the course of the experiment; therefore, all treatments were pooled. There was a significant ($P<0.002$) effect of period on weight loss in which the most severe drop in animal weights occurred in the post-transit period. Animals in all treatment groups lost weight after transportation and gradually gained weight during the recovery periods. Although not significantly, animals in the outside control, 10 mg MGA and 50 mg progesterone groups tended to gain the most weight during the recovery period. Changes in body weight for all treatment groups over the different periods of the experiment are shown in FIG. 6.

Hematological Changes

There was no significant effect due to treatment on any of the hematological parameters evaluated; therefore, all treatments were pooled. An analysis by period of the hematological profiles indicated an increase ($P<0.05$) in the RBC and WBC counts after transportation and an increase in RBC's after confinement (Table I). A small but significant decrease ($P<0.05$) was seen in PCV during confinement and after transport.

Differential leukocyte counts indicated a typical response for stressed beef calves. A significant period effect ($P<0.0001$) was observed for neutrophils, lymphocytes, eosinophils, and monocytes. During confinement, there was a significant increase ($P<0.05$) in neutrophil numbers and a decrease ($P<0.05$) in eosinophil numbers and in the neutrophil:lymphocyte ratio ($P<0.05$). Compared to pretreatment (preconfinement) values, there was an increase ($P<0.05$) in the number of neutrophils in the circulation following transportation. Transportation caused a decrease in lymphocytes, eosinophils, and monocytes in peripheral blood from all calves regardless of treatment groups. Over all treatment groups there was a further decrease ($P<0.05$) in the leukocyte:neutrophil ratio compared to treatment levels. The effect of period of stress on leukocyte populations for all treatment groups combined in shown in Table II.

TABLE I

Effects on WBC, RBC, and PCV Due to Different Periods of Stress[1]

| | Pretreatment | Treatment/ Confinement | Post-transit |
|---|---|---|---|
| RBC[2] | 73.8 ± 1.45[a] | 89.3 ± 1.46[b] | 84.8 ± 1.25[c] |
| WBC[3] | 10.3 ± 0.45[a] | 10.8 ± 0.39[a] | 12.8 ± 0.36[b] |
| PCV | 38.3 ± 0.40[a] | 36.7 ± 0.48[b] | 36.0 ± 0.42[b] |

[1]Values with different superscripts vary significantly. Values indicate the mean of 60 observations ± SEM.
[2]($\times 10^6$)
[3]($\times 10^3$)

Blood Chemistry

Lactate levels were unaffected by treatment; however, a significant period effect ($P<0.0002$) was observed in which highest levels occurred during the pretreatment period, after which they declined. Pyruvate levels were also not affected by treatment, but a significant period effect ($P<0.002$) occurred in which levels were highest during the pretreatment phase, after which a nonsignificant drop occurred during the treatment period and continued to drop during the post-transit period. A trend similar to that for lactate was also seen when the data were analyzed as the ratio of lactate to pyruvate. Glucose levels were unaffected by either treatment or period. Values for lactate, pyruvate, and glucose are summarized in Table III.

Lymphocyte Response to Mitogens

Figure 7:
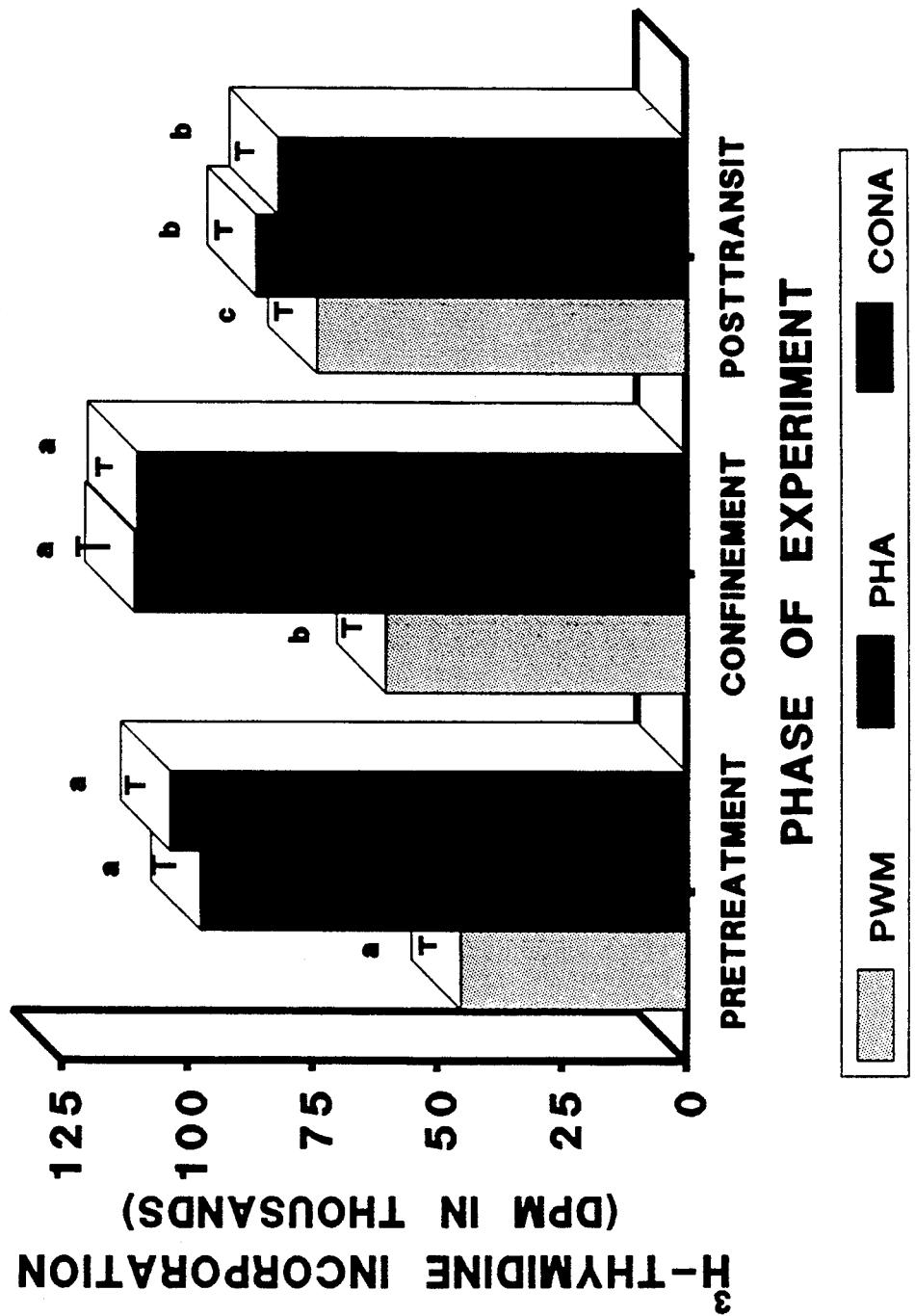
FIG. 7 shows the proliferative responses of bovine peripheral blood lymphocytes to PWM, PHA, and Con A in Example 2.

A significant period effect ($P<0.002$) was seen in the proliferative responses of peripheral lymphocytes to the T-cell mitogens Con A and PHA, which were greater during the pretreatment and treatment periods ($P<0.05$) than during the post-transit period. T-dependent B-cell responses, as indicated by the proliferation of lymphocytes by PWM, was significantly influenced by period ($P<0.0001$) but not by treatment. The proliferation of lymphocytes by PWM increased during the treatment period and after transportation as compared to the pretreatment period ($P<0.05$). FIG. 7 summarizes lymphocyte response to each mitogen over the different periods of the experiment. For each respective mitogen, different letters appearing above the standard error bars denote a significant difference between periods.

Antibody Cell-Mediated Cytotoxicity

The efficiency of polymorphonuclear cells in causing lysis of target cells was measured by antibody cell-mediated cytotoxicity.

TABLE II

Effect of Stress on Leukocyte Number (cells/mm[3])[1]

| | Pretreatment | Treatment/ Confinement | Post-transit |
|---|---|---|---|
| Neutrophils | 2662 ± 216[a] | 3231 ± 197[b] | 5936 ± 261[b] |
| Eosinophils | 142 ± 15[a] | 89 ± 18[b] | 82 ± 18[b] |
| Monocytes | 410 ± 27[a] | 405 ± 34[a] | 326 ± 29[b] |
| Lymphocytes | 7121 ± 334[a] | 7050 ± 291[a,b] | 6410 ± 242[b] |
| Lymphocyte/ Neutrophil | 3.6 ± 0.4[a] | 2.6 ± 0.2[b] | 1.3 ± 0.1[c] |

Values with different superscripts across rows vary significantly at the $P < 0.05$ level. Values indicate the mean of 60 observations ± SEM.

TABLE III

Effects on Lactate, Pyruvate, L/P Ratio and Glucose Due to Different Periods of Stress[1]

|  | Pretreatment | Treatment/Confinement | Post-transit |
|---|---|---|---|
| Lactate | $4.9 \pm 0.40^a$ | $2.3 \pm 0.18^b$ | $3.0 \pm 0.28^b$ |
| Pyruvate | $0.17 \pm 0.01^a$ | $0.12 \pm 0.01^b$ | $0.15 \pm 0.01^a$ |
| L/P Ratio | $28.4 \pm 1.38^a$ | $20.2 \pm 1.21^b$ | $20.3 \pm 1.03^b$ |
| Glucose (mg/dl) | $98.9 \pm 2.7$ | $101.8 \pm 2.1$ | $102.8 \pm 2.0$ |

[1]Values with different superscripts across rows vary significantly ($p < 0.05$). Values indicate the mean of 60 observations ± SEM.

Figure 8:
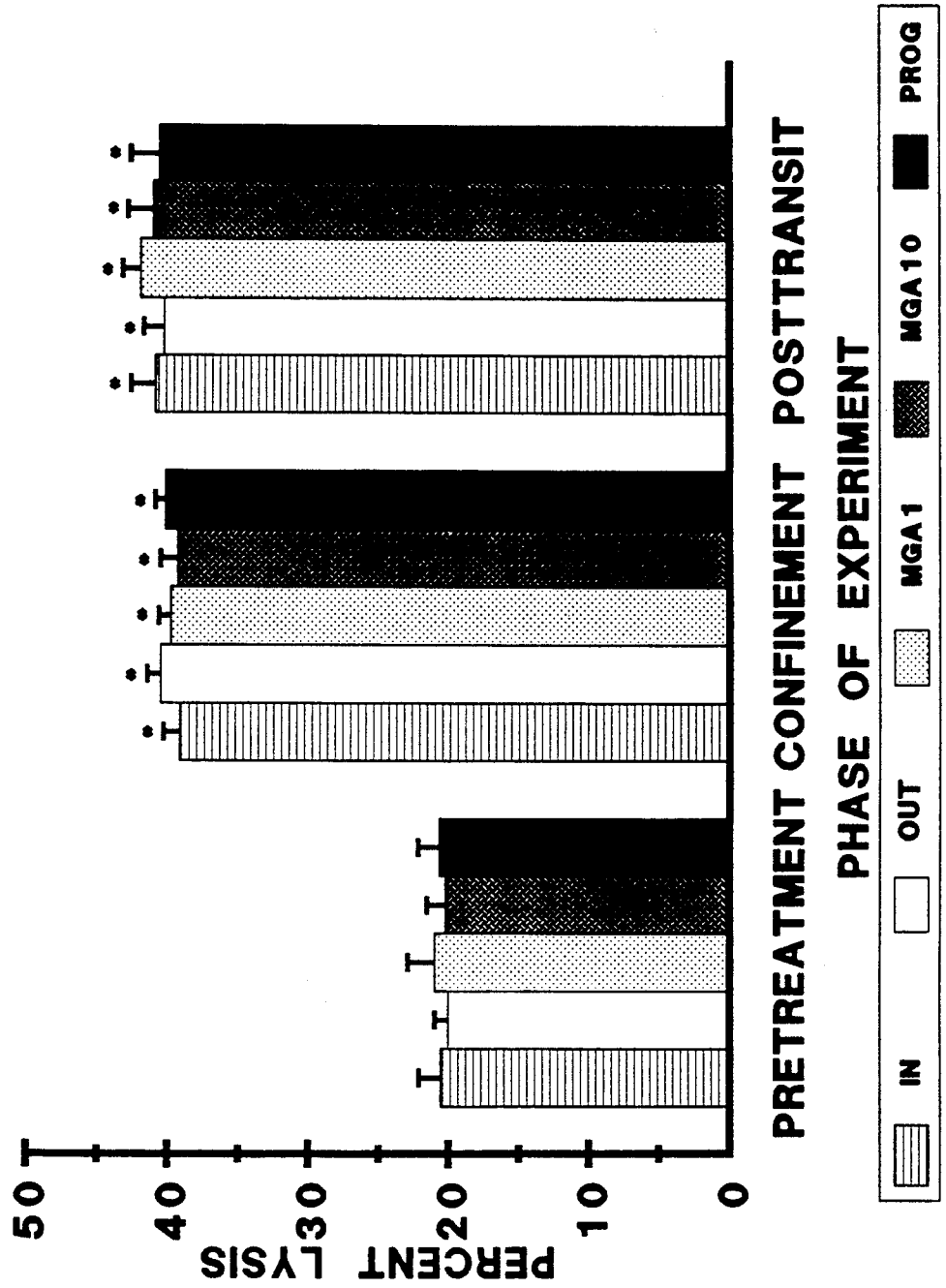
FIG. 8 shows antibody-dependent cell-mediated cytotoxicity of polymorphonuclear cells from calves during periods of stress in Example 2.

No treatment effect was observed; however, a significant effect ($P < 0.0001$) or period was clearly seen (FIG. 8). In the Figure, bars represent mean values. Bars marked with an asterisk (*) differed significantly from the pretreatment phase of the experiment. Activity of the PMN's increased during the treatment period and after transportation compared to the pretreatment values.

Antibody Response and Lymphocyte Proliferation in Response to *Brucella abortus*

Figure 9:
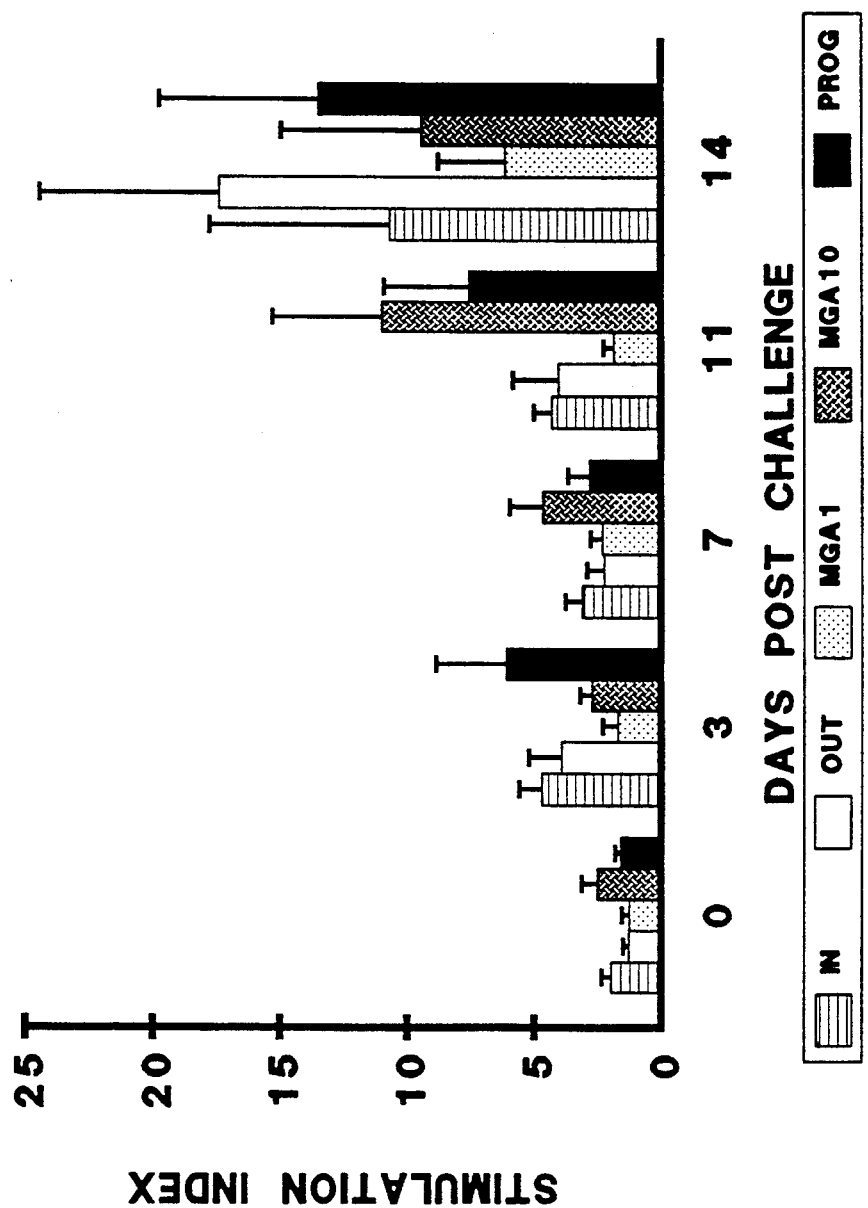
FIG. 9 shows the response of bovine peripheral blood lymphocytes to Brucella antigen in Example 2.

The response of calves to injection with Brucella antigen strain 19 directly before transport was measured in proliferating peripheral blood lymphocytes obtained on days 0, 3, 7, 11, and 14, at which time lymphocytes were cultured with Brucella antigen in vitro. There was no significant overall treatment effect on the stimulation index of lymphocytes in response to culture with Brucella antigen in vitro; however, a treatment X time interaction was seen ($P < 0.04$). There was a tendency for the 1 mg MGA group to have the lowest response among the different treatment groups, and for the outside control and progesterone treatment groups to have the highest response (FIG. 9). In the Figure, bars represent mean values ± SEM. Over all treatments a significant ($P < 0.0001$) effect over time was also observed for lymphocyte stimulation in response to Brucella challenge in vitro.

The level of Brucella specific IgM and IgG was unaffected by treatment. However, antibody levels were significantly influenced by time ($P < 0.0001$) after injection of Brucella antigen (Table IV).

Data from the present study indicates that, in general, the administration of progesterone or the synthetic progestin MGA at low levels had little effect on immune function of the stressed beef calf. In contrast, the effect of confinement and transportation had a significant influence on the beef calf's immunological responses.

It is understood that the foregoing detailed description is given merely by way of illustration and that modifications and variations may be made therein without departing from the spirit and scope of the invention.

TABLE IV

Changes in Immunoglobulin After Initial Exposure to Brucella Antigen

| Days After Exposure to Brucella | IgM | IgG |
|---|---|---|
| 3 | $0.328 \pm 0.046^a$ | $0.057 \pm 0.014^a$ |
| 7 | $0.758 \pm 0.072^b$ | $0.235 \pm 0.013^c$ |
| 11 | $0.642 \pm 0.069^b$ | $0.140 \pm 0.025^b$ |
| 14 | $0.624 \pm 0.070^b$ | $0.371 \pm 0.028^d$ |

Mean ± SEM: means having different superscripts within columns are different at the $p < 0.05$ level.
Number of observation per day = 30.
IgM and IgG specific antibody to Brucella was not detectable on day 0 (day of Brucella strain 19 injection).
Values represent change in optical density at 15 min as measured by Elisa.

I claim:

1. A method for decreasing hypersecretion of glucocorticoids in male livestock and/or decreasing basal levels of glucocorticoids in male castrated livestock selected from the group of bovine and sheep, without impairing immune response comprising:
   a. administering melengesterol acetate or derivatives thereof to said male livestock at a dosage effective to substantially decrease the secretion of cortisol without substantially suppressing immune response.

2. A method as described in claim 1, wherein said melengesterol acetate or derivative thereof is administered orally and said dosage is between about 1 mg/head/day and about 50 mg/head/day.

3. A method as described in claim 2, wherein said melengesterol acetate or derivative thereof is administered orally and said dosage is between about 1 mg/head/day and about 10 mg/head/day.

4. A method as described in claim 1, wherein said livestock are castrated.

5. A method as described in claim 1, wherein said melengesterol acetate is administered to said livestock about 1-7 days before periods of stress.

6. A method as described in claim 1, wherein said melengesterol acetate is administered to said livestock about 5-7 days before periods of stress.

7. A method as described in claim 1 wherein said livestock are bovine.

8. A method as described in claim 7 wherein said bovine livestock are steers.

9. A method as described in claim 1 wherein said livestock are sheep.

10. A method as described in claim 1 wherein said dosage is effective to substantially decrease but not prevent the secretion of cortisol.

11. A method as described in claim 1 wherein said melengesterol acetate or derivative thereof is administered orally.

12. A method as described in claim 11 wherein said melengesterol acetate or derivative thereof is administered in admixture with feed.

* * * * *